United States Patent
Souvie et al.

(10) Patent No.: US 6,774,259 B2
(45) Date of Patent: Aug. 10, 2004

(54) METHOD FOR SYNTHESIS OF N-[(S)]-1-CARBOXYBUTYL-(S)-ALANINE ESTERS AND USE IN SYNTHESIS OF PERINDOPRIL

(75) Inventors: Jean-Claude Souvie, Le Havre (FR); Alain Renaud, Rouen (FR)

(73) Assignee: Les Laboratoires Servier, Courbevoie (FR)

( * ) Notice: Subject to any disclaimer, the term of this patent is extended or adjusted under 35 U.S.C. 154(b) by 80 days.

(21) Appl. No.: 10/257,239

(22) PCT Filed: Apr. 10, 2001

(86) PCT No.: PCT/FR01/01088
§ 371 (c)(1),
(2), (4) Date: Oct. 9, 2002

(87) PCT Pub. No.: WO01/56972
PCT Pub. Date: Aug. 9, 2001

(65) Prior Publication Data
US 2003/0109743 A1 Jun. 12, 2003

(30) Foreign Application Priority Data
Apr. 11, 2000 (FR) .............................. 00 04610

(51) Int. Cl.⁷ ............................................ C07C 229/00
(52) U.S. Cl. ........................ 560/171; 560/155; 562/571
(58) Field of Search .............................. 560/155, 171; 562/571

(56) References Cited

U.S. PATENT DOCUMENTS

| | | | | | |
|---|---|---|---|---|---|
| 4,296,110 A | * | 10/1981 | Johnson | ...................... | 424/244 |
| 4,344,949 A | * | 8/1982 | Hoefle et al. | ................ | 424/258 |
| 4,503,043 A | * | 3/1985 | Blankley | ....................... | 514/10 |
| 4,902,817 A | * | 2/1990 | Vincent et al. | ............. | 560/171 |
| 4,914,214 A | * | 4/1990 | Vincent et al. | ............. | 548/492 |

* cited by examiner

*Primary Examiner*—Ba K. Trinh
*Assistant Examiner*—Taylor V. Oh
(74) *Attorney, Agent, or Firm*—The Firm of Hueschen and Sage

(57) ABSTRACT

A stereoselective process for the industrial synthesis of compounds of formula (I):

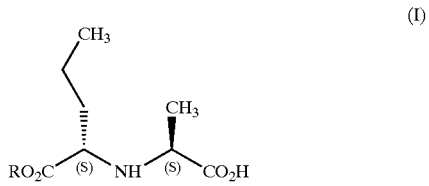

wherein R represents linear or branched ($C_1$–$C_6$)alkyl, and application in the synthesis of perindopril and pharmaceutically acceptable salts thereof.

6 Claims, No Drawings

METHOD FOR SYNTHESIS OF N-[(S)]-1-CARBOXYBUTYL-(S)-ALANINE ESTERS AND USE IN SYNTHESIS OF PERINDOPRIL

The present invention relates to a process for the industrial synthesis of N-[(S)-1-carboxybutyl]-(S)-alanine esters, and to their application in the industrial synthesis of perindopril and its pharmaceutically acceptable salts.

More specifically, the present invention relates to a new process for the industrial synthesis of the compounds of formula (I):

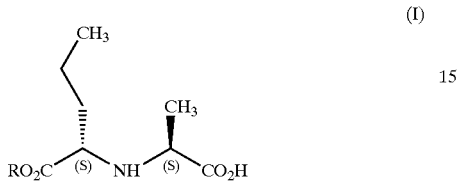

wherein R represents a linear or branched $(C_1-C_6)$alkyl group,
and addition salts thereof with a mineral or organic acid or base.

The compounds of formula (I) obtained in accordance with the process of the invention are useful in the synthesis of perindopril of formula (II):

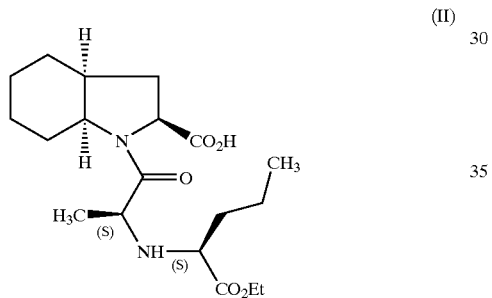

and in the synthesis of pharmaceutically acceptable salts thereof.

Perindopril and salts thereof have valuable pharmacological properties. Their principal property lies in the inhibition of the enzyme that converts angiotensin I (or kininase II), which enables on the one hand prevention of the conversion of the decapeptide angiotensin I to the octapeptide angiotensin II (vasoconstrictor) and on the other hand prevention of the degradation of bradykinin (vasodilator) to inactive peptide. Those two actions contribute to the beneficial effects of perindopril in cardiovascular disorders, especially arterial hypertension and cardiac insufficiency.

Perindopril, its preparation and its therapeutic use have been described in European Patent Specification EP 0 049 658.

Given the pharmaceutical interest in that compound, it is important to be able to obtain the intermediate of formula (I) by an effective industrial synthesising process that allows in particular the selective production of the (S,S) diastereoisomer in a good yield and with an excellent degree of purity.

Some methods for the preparation of the compounds of formula (I) are already known, but on an industrial scale those processes have significant disadvantages:

The journal Tet. Lett. 1982, 23 (16), 1677–80 describes the production of a compound of formula (I) (R=ethyl) by reacting ethyl 2-oxovalerate with alanine tert-butyl ester in ethanol in the presence of sodium cyanoborohydride, but that reducing agent is particularly toxic, very hygroscopic and difficult to handle on an industrial scale.

The patent specifications EP 0 308 340 and EP 0 308 341 describe the production of a compound of formula (I) (R=ethyl) by reacting ethyl norvalinate hydrochloride with pyruvic acid in water in the presence of hydrogen, palladium-on-carbon and sodium hydroxide. The isolation of the crude product is then carried out by evaporation of the water, then ethanol is added to precipitate the sodium chloride formed during the reaction. After filtration, the ethanol solution obtained is evaporated and the residue is recrystallized from acetonitrile.

That process has several disadvantages:
In view of the fact that pyruvic acid is unstable, its use generates impurities in the reaction mixture.
The reaction occurs at a pH close to neutral. The use of ethyl norvalinate hydrochloride thus necessitates the addition of a significant amount of sodium hydroxide (from 1.1 to 1.2 mol per mol of norvalinate hydrochloride employed), which generates an appreciable amount of sodium chloride, the removal of which is laborious on isolation on an industrial-scale.
The isolation comprises an evaporation step for the removal of water from the reaction mixture which, on that scale, takes an especially long time.

The patent specification EP 0 309 324 describes obtaining a compound of formula (I) (R=ethyl) by reacting alanine benzyl ester with ethyl α-bromovalerate in dimethylformamide in the presence of triethylamine. The major drawbacks of that process are the large number of steps involved and the low yield of the (S,S) isomer. Indeed, since the reaction is not diastereoselective, in order to obtain the pure (S,S) isomer it requires the addition of a purification step, which comprises fractional crystallization in the presence of maleic acid.

The Applicant has now developed a process for the industrial synthesis of the compounds of formula (I) that is of great interest, first because it allows the (S,S) diastereoisomer to be obtained directly with very good purity and in a good yield, secondly because the isolation is particularly quick and simple to perform on an industrial scale, and finally because it uses alanine as the source of chirality, a starting material that is natural and hence low in cost.

More specifically, the present invention relates to a process or the industrial synthesis of compounds of formula (I) which is characterized in that alanine of formula (III):

is condensed with a compound of formula (IV):

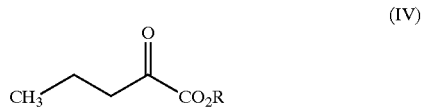

wherein R is as defined for formula (I),
with hydrogenation which is catalyzed by 5% palladium-on-carbon, in water, at a pressure of from 1 to 30 bar, preferably from 1 to 5 bar, at a temperature of from 10 to 60° C., preferably from 10 to 40° C., in the presence of sodium hydroxide in an amount of from 0 to 0.5 mol, preferably from 0.1 to 0.2 mol, per mol of compound of formula (IV) employed, in order to yield the compound of formula (I) in optically pure form following acidification of the reaction mixture to a pH of from 3 to 3.5, filtration, and recrystallization of the resulting precipitate from acetonitrile.

The small amount of sodium hydroxide used in the process limits the formation of sodium chloride in the acidification of the reaction mixture, thereby facilitating later recrystallization.

The isolation avoids the total evaporation of water from the reaction mixture and is particularly quick and simple to perform on an industrial scale.

The Example below illustrates the invention but does not limit it in any way.

EXAMPLE

N-[(S)-Ethoxycarbonyl-1-Butyl]-(S)-Alanine

Into a tank, fitted with a stirrer, introduce 25 kg of L-alanine dissolved in water, 1.1 kg of sodium hydroxide and 36 kg of ethyl 2-oxopentanoate. Stir the reaction mixture for 30 minutes. Into a hydrogenation apparatus introduce 5% palladium-on-carbon suspended in water, then the mixture obtained above. Hydrogenate at ambient temperature at a pressure of 1 bar until the theoretical amount of hydrogen has been absorbed. Remove the catalyst by filtration, then add concentrated hydrochloric acid to the filtrate until a pH of 3 is obtained. Harvest the resulting solid by means of filtration, take up the cake in acetonitrile at reflux, filter while hot and then allow to crystallize.

What is claimed is:

1. A process for the synthesis of a compound of formula (I)

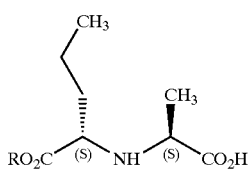

wherein R represents a linear or branched $(C_1–C_6)$alkyl, wherein alanine of formula (III):

is condensed with a compound of formula (IV):

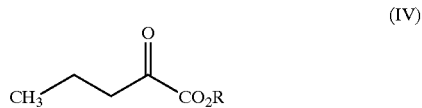

wherein R is as defined for formula (I),
with hydrogenation which is catalyzed by 5% palladium-on-carbon, in water,
at a pressure of 1 to 30 bar,
at a temperature of 10 to 60° C.,
in the presence of sodium hydroxide in an amount of up to 0.5 mol/mol of a compound of formula (IV),
and the reaction mixture is then acidified to a pH of 3 to 3.5,
to yield a precipitate,
which is filtered and recrystallized from acetonitrile,
to yield the compound of formula (I) in optically pure form.

2. The process of claim 1, for producing the compound of formula (I) wherein R represents ethyl.

3. The process of claim 1, wherein the hydrogenation pressure is 1 to 5 bar.

4. The process of claim 1, wherein the hydrogenation temperature is 10 to 40° C.

5. The process of claim 1, wherein the amount of sodium hydroxide added is 0.1 to 0.2 mol per mol of the compound of formula (IV) employed.

6. A process for the synthesis of perindopril or pharmaceutically acceptable salt thereof, using a compound of formula (I) that is obtained according to the process of claim 1.

* * * * *

UNITED STATES PATENT AND TRADEMARK OFFICE
CERTIFICATE OF CORRECTION

PATENT NO. : 6,774,259 B2
DATED : August 10, 2004
INVENTOR(S) : Jean-Claude Souvie et al.

It is certified that error appears in the above-identified patent and that said Letters Patent is hereby corrected as shown below:

Title page,
Item [54], Title, "METHOD FOR SYNTHESIS OF N-[(S)]-1-CARBOXYBUTYL-(S)-ALANINE ESTERS AND USE IN SYNTHESIS OF PERINDOPRIL" should be -- METHOD FOR SYNTHESIS OF N-[(S)-1-CARBOXYBUTYL]-(S)-ALANINE ESTERS AND USE IN SYNTHESIS OF PERINDOPRIL --

Signed and Sealed this

Fourteenth Day of December, 2004

JON W. DUDAS
*Director of the United States Patent and Trademark Office*